United States Patent
Buerger et al.

(10) Patent No.: US 10,869,723 B2
(45) Date of Patent: Dec. 22, 2020

(54) DETERMINING AN OPTIMAL PLACEMENT OF A PEDICLE SCREW

(71) Applicant: KONINKLIJKE PHILIPS N.V., Eindhoven (NL)

(72) Inventors: Christian Buerger, Hamburg (DE); Christian Lorenz, Hamburg (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 101 days.

(21) Appl. No.: 16/096,367

(22) PCT Filed: Apr. 26, 2017

(86) PCT No.: PCT/EP2017/059941
§ 371 (c)(1),
(2) Date: Oct. 25, 2018

(87) PCT Pub. No.: WO2017/186799
PCT Pub. Date: Nov. 2, 2017

(65) Prior Publication Data
US 2019/0133690 A1 May 9, 2019

(30) Foreign Application Priority Data
Apr. 28, 2016 (EP) .................................. 16167393

(51) Int. Cl.
*A61B 34/10* (2016.01)
*A61B 17/17* (2006.01)
(Continued)

(52) U.S. Cl.
CPC .......... *A61B 34/10* (2016.02); *A61B 17/1757* (2013.01); *A61B 17/7076* (2013.01);
(Continued)

(58) Field of Classification Search
CPC ........ A61B 2034/102; A61B 2034/101; A61B 2034/107; A61B 2034/105; A61B 34/10
See application file for complete search history.

(56) References Cited

U.S. PATENT DOCUMENTS

| | | |
|---|---|---|
| 7,194,120 B2 | 3/2007 | Wicker |
| 7,623,902 B2 | 11/2009 | Pacheco |

(Continued)

FOREIGN PATENT DOCUMENTS

| | | |
|---|---|---|
| CN | 103099669 A | 3/2013 |
| CN | 103976790 A | 8/2014 |

(Continued)

OTHER PUBLICATIONS

Ecabert, Olivier, et al. "Automatic Model-Based Segmentation of the Heart in CT Images." Medical Imaging, IEEE Transactions on Sep. 27, 2008: 1189-1201.

(Continued)

*Primary Examiner* — Julianna N Harvey (57) ABSTRACT

The present invention relates to a device (2) for determining an optimal placement of a pedicle screw (4), comprising a processing unit (14), wherein the processing unit is configured to receive a model data set representing a model surface (22) of a human vertebra model (18) and a pedicle screw model (30) being optimally placed in a span of a pedicle section (28) of the model surface, wherein the processing unit is configured to receive 5 image data representing a surface image (26) of at least one human vertebra (6), GO and wherein the processing unit is configured to adapt the model data set for each of a number of the at least one human vertebra, such that an adapted model data set representing a correspondingly adapted model surface (36), which fits to the surface image of the respective human vertebra, is provided for each of the number of the at least one human vertebra, wherein each of the 10 adapted model data sets (Continued)

also represents a correspondingly adapted pedicle screw model (38). The present invention further relates to a corresponding method, a corresponding computer program element and a corresponding computer readable medium.

11 Claims, 8 Drawing Sheets

(51) Int. Cl.
*A61B 17/70* (2006.01)
*A61B 90/00* (2016.01)
*A61B 17/56* (2006.01)

(52) U.S. Cl.
CPC ... *A61B 2017/564* (2013.01); *A61B 2034/102* (2016.02); *A61B 2034/105* (2016.02); *A61B 2034/107* (2016.02); *A61B 2090/364* (2016.02); *A61B 2090/365* (2016.02)

(56) References Cited

U.S. PATENT DOCUMENTS

| | | |
|---|---|---|
| 9,119,670 B2 | 9/2015 | Yang |
| 2007/0270680 A1 | 11/2007 | Sheffer |

FOREIGN PATENT DOCUMENTS

| | | |
|---|---|---|
| KR | 1264198 B1 | 5/2013 |
| KR | 1547608 B1 | 8/2015 |
| WO | 2005081863 A2 | 9/2005 |
| WO | 2006092600 A1 | 9/2006 |
| WO | 2008027860 A2 | 3/2008 |

OTHER PUBLICATIONS

Rasche, V. et al., "3D Rotational X-ray Imaging (3D-RX) for the Depiction of the Trabecular Bone Structure", International Congress Series, vol. 1281, pp. 159-163, 2005.

Weese. J. et al "Shape Constrained Deformable Models for 3D Medical Image Segmentation", Information Processing in Medical Imaging, pp. 380-387, 2001.

DETERMINING AN OPTIMAL PLACEMENT OF A PEDICLE SCREW

CROSS-REFERENCE TO PRIOR APPLICATIONS

This application is the U.S. National Phase application under 35 U.S.C. §371 of International Application No. PCT/EP2017/059941, filed on Apr. 26, 2017, which claims the benefit of European Patent Application No. 16167393.4, filed on Apr. 28, 2016. These applications are hereby incorporated by reference herein.

FIELD OF THE INVENTION

The present invention relates to a device and a method for determining an optimal placement of a pedicle screw, a respective computer program element and a computer-readable medium.

BACKGROUND OF THE INVENTION

A spinal column is a complex system of bones and connective tissues. The spinal column provides support for the body and protects the spinal cord and associated nerves, in particular from damage. The spinal column comprises a series of vertebra, also referred to as human vertebra, stacked upon one another. An intervertebral disk is situated between each vertebral body that cushions and dampens compressive forces experienced by the spinal column.

A technique commonly referred to as spinal fusion or spinal fixation is often used as a treatment of spinal column maladies. Such spinal column maladies may include disorders caused by abnormalities, diseases or trauma. For spinal fusion, surgical implants are used for fusing together and/or mechanically immobilizing vertebra of the spine. In particular, metal screws are inserted through the patient's back into the vertebra and screws of adjacent vertebra are connected by metal rods to generate fixed bridges. Such spinal fusions have been used effectively to treat the above-described spinal column maladies. However, there are disadvantages associated with the current surgical implants. Such disadvantages may relate to the accurate measure of the size of the surgical implant, for instance the above stated metal screw. A further disadvantage may relate to the accurate placement of a surgical implant.

Document U.S. Pat. No. 7,194,120 B2 relates to a method and a system for image-guided placement of implants. Medical image data is obtained from one or more medical imaging devices at least representing a part of the spinal column. Further, surface boundaries of the bone structure are determined based on the medical image data. Furthermore, an optimal trajectory of the pedicle screw having a predetermined initial diameter within the surface boundaries is calculated when the optimal trajectory is automatically calculated to be within the surface boundaries by the computer process performing an algorithm mathematically comparing the surface boundaries on a computer.

WO 2006/092600 A1 discloses a computer implemented method for automatically planning at least a part of a surgical procedure to be carried out on a body part of a patient. A virtual model of the body part is provided having data associated with it representing at least a part of a planned surgical procedure, such as a representation of a component of hardware which is to be used in the procedure, for example a surgical instrument and implant. The virtual model is morphed using data derived from the patient's real body part thereby also adapting the part of the planned surgical procedure to reflect the anatomy of the patient's real body part.

However, there are some disadvantages associated with the current methods for planning of guided placement of implants, in particular placement of pedicle screws into a vertebra.

SUMMARY OF THE INVENTION

There may be a need for a less complex determination for an optimal placement of a pedicle screw within a vertebra. In particular, a respective determination should be reproducible, be available to automatic use and should provide patient-specific data serving as a basis for an optimal placement of the pedicle screw without damaging the respective vertebra.

The object of the present invention is solved by the subject-matter of the independent claims, wherein further embodiments are incorporated in the dependent claims.

According to a first aspect of the present invention, a device for planning a placement of pedicle screws is provided. The device comprises a processing unit. The processing unit is configured to receive a global model data set, which represents a first model surface of a first human vertebra and a first pedicle screw model positioned in a pedicle section of the first model surface, a second model surface of a second human vertebra and a second pedicle screw model positioned in a pedicle section of the second model surface, and a model arrangement of the first vertebra relative to the second vertebra.

The processing unit is further configured to receive image data representing at least a first image of the first human vertebra, a second image of the second human vertebra and an arrangement of the first image relative to the second image.

The processing unit is further configured to adapt the global model data set to the image data, the adapted model data set representing a first adapted model surface adapted to the first image of the first human vertebra, a second adapted model surface adapted to the second image of the second human vertebra, and a correspondingly adapted model arrangement of the first adapted model surface relative to the second adapted model surface. The adapted model data set further represents correspondingly adapted first and second pedicle screw models.

The global model set is thus a set of data comprising a subset of data representing at least model surfaces of a first and second human vertebra. The subset of data may represent a grid or a mesh of points representing the model surface of the human vertebra model. Thus, the model surface may represent a surface of the human vertebra model.

The model data set further represents a pedicle screw model. Thus, the model data set may comprise data representing a model surface of the pedicle screw or at least points of a surface of the pedicle screw model, for instance representing an end section of the pedicle screw model and/or its direction.

The pedicle screw model is positioned in a pedicle section of the model surface of the human vertebra model.

Hereinafter, the "span" of the model surface refers to the interior space enclosed or encompassed by the model surface. In particular, the span of a pedicle section of the model surface preferably refers to the interior space surrounded or encompassed by the pedicle section of the model surface.

Accordingly, the model data set provides the information where and how the pedicle screw model is arranged with respect to the models surface of the human vertebra model. For instance, if the pedicle screw model is represented by two points, preferably each defining an end of a pedicle screw, which the pedicle screw model is supposed to represent, at least one of the two points is located within the span of the model surface of the human vertebra model. Further, the two points represent a direction of the pedicle screw model in regard to the model surface of the human vertebra model. The second point is preferably located outside the model surface of the human vertebra model. In practice, a pedicle screw is used to anchor other surgical devices, in particular rods. As such, a pedicle screw should be placed with precision in the pedicle of a real human vertebra to avoid damaging of the pedicle structure and provide at the same time a good anchor effect.

The optimal placement of the pedicle screw model may refer to a predetermined placement of the pedicle screw model. The predetermined placement of the pedicle screw model may result in an advantageous compromise between an anchor effect and a damaging-prevention of a pedicle screw, if a real pedicle screw is placed in a pedicle of a real human pedicle based on the information of the model data set, in particular based on respectively represented pedicle screw model, wherein the model surface fits to the surface image of the real human pedicle.

For example, from historical data representing previous pedicle screw placement procedures, an optimal placement of a pedicle screw can be predetermined, which predetermined placement can then be encoded in the model data set. Similarly, based on the statistical data regarding an average human vertebra shape, a model surface of a human vertebra model can be determined.

The processing unit is configured to receive image data representing images of at least the first and second human vertebrae. The image data may be obtained by one or more medical imaging devices, such as computer tomography (CT), magnetic resonance imaging (MRI), positron emission tomography (PET), stereotactic ultrasound, endoscopic ultrasound, and/or other medical imaging devices, such as a C-arm imaging device.

In particular, the model data set may be adapted to image data representing the shape of the vertebrae in an actual subject. In this respect, "adaptation" refers to a segmentation of the image data based on the respective model, whereby the model data are for example elastically deformed to obtain a best fit of the model surfaces with the vertebrae images in the image data.

This adaptation involves techniques well known in the art, see for example an article "Shape Constrained Deformable Models for 3D Medical Image Segmentation" by J. Weese et al., Information Processing in Medical Imaging 2001, pp. 380-387, Lecture Notes in Computer Science, vol 2082, Springer, Berlin, Heidelberg.

In a preferred embodiment, the adaptation involves not only an adaptation of "local" vertebra models to the corresponding vertebrae in the image, but also a global adaptation of a model arrangement of the first adapted model surface relative to the second adapted model surface. That is, the global model data set also includes data regarding the relative spatial arrangement of individual vertebrae of the human spine with respect to each other. This model arrangement data is likewise used during adaptation as an extra parameter For example, the model arrangement data may comprise data about the distance between the two respective human vertebrae, such as a distance between corresponding processes of the two human vertebra, or a twist angle of the first human vertebra relative to the second human vertebra. A model distance may be defined for one or more vertebra processes, such as the spinous process, the transverse process and/or the superior and inferior articular processes. By deriving corresponding parameters for an actual patient from image data, the model arrangement data serves as an additional constraint in the adaptation of the global model data set to the image data.

Alternatively or in addition, the model arrangement data may comprise coordinate data for specific vertebra points, such as one or more vertebra processes, in a global coordinate system representing the human spine.

As an effect, a desired placement for pedicle screws in the first and second vertebrae, which are preferably adjacent vertebrae of the human spine, is provided without a subsequent calculation. Instead, the predetermined placement of the pedicle screw model is adapted together with the model surfaces, such that after adaptation, adapted pedicle screw models are suitably positioned with respect to the adapted model surfaces.

Instead of separately calculating the optimal placement of the pedicle screw model for multiple vertebrae, a single adaptation of the global model data set is sufficient, in order to provide the planning information for the optimal placement of pedicle screws in particular in adjacent vertebrae. Based on this planning information, a subsequent procedure of positioning real pedicle screws in corresponding real human vertebrae can be carried out.

According to a preferred embodiment, the global model data set further represents a connecting rod model extending from the first screw model to the second screw model, wherein the processing unit is configured to adapt the connecting rod model based on the adaptation of the arrangement resulting in an adapted connecting rod model extending from the first adapted screw model to the second adapted screw model, and wherein the adapted global model data set further represents the adapted connecting rod model.

The connecting rod model may represent the information for a real connecting rod connecting a first screw and a second screw, wherein the first screw model is used for placing a first screw in a first human vertebra relating to the first surface image and wherein the second screw model is used for placing a second screw in a second human vertebra relating to the second surface image.

As a result of adapting the global model data set, a respective adaptation is carried out for the connecting rod model. Thus, the adapted connecting rod model remains optimal. A subsequent calculation for a connecting rod can be prevented. Instead, the adaptation being carried out provides all necessary information for the placement of the pedicle screws as well as the connecting rod for connecting the two pedicle screws subsequent to their insertion.

According to an exemplary embodiment, a first end section of the pedicle screw model, represented by the model data set, is located within the span of the respective model surface of the human vertebra model and a second end section of the pedicle screw model, also represented by the model data set, protrudes out of the model surface of the human vertebra model.

According to a preferred embodiment, the pedicle screw model, represented by the model data set, is arranged with respect to the respective model surface of the human vertebra model, such that the second end section of the pedicle screw model is arranged between two, outwardly extending surface sections of the model surface representing processes of the human vertebra model.

The processes of the human vertebra model preferably relate to the spinous process and the traverse process. Thus, one of the outwardly extending surface sections of the model surface may represent the spinous process. The other outwardly extending surface section of the model surface may represent the traverse process of the human vertebra model.

According to a further embodiment, the pedicle screw model, represented by the model data set, is arranged with respect to the respective model surface of the human vertebra model, such that the second end section of the pedicle screw model is not in vertical overlap with one of the outwardly extending surface sections of the model surface representing the processes of the human vertebra model.

On a detail consideration, a vertebra may comprise more than the above named processes. In order to place a connection rod directly without intersecting one of the processes of a human vertebra, the second end section of the pedicle screw model is arranged, such that it does not overlap with one of the outwardly extending surface sections of the model surface of the human vertebra model. This will remain after the adaption of the model data set. As an effect, connection rods can be placed without any conflict between two pedicle screws, when using the model data set as an information basis for placing the pedicle screws and the rods.

According to a preferred embodiment, the model data set represents the pedicle screw model at least by two of: a virtual entry point of the pedicle screw model into the span of the model surface of the human vertebra model, a direction of the pedicle screw model with respect to the model surface of the human vertebra model, and a virtual exit point of the pedicle screw model out of the span of the model surface of the human vertebra model.

For instance, the model data set represents the pedicle screw model at least by a virtual entry point of the pedicle screw model into the span of the model surface of the human vertebra model. Thus, the model data set provides the information for an entry point at the surface of a human vertebra, where a real pedicle screw has to enter the human vertebra. Accordingly, the virtual entry point relates to the information, where a pedicle screw intersects the surface of the human vertebra. Further, the entry point may relate to the model surface at a section thereof, such that the direction of the pedicle screw model is in an angle between 80° and 110° to said surface section. As an effect, a head of a real pedicle screw can be easily place a corresponding surface section of a real human vertebra, if the placement is carried out on the respective information provided by the model data set or the adapted model data set, respectively. When adapting the model data set, the virtual entry point is correspondingly adapted. Thus, the adapted model data set represents a correspondingly adapted virtual entry point, which provides the information for an optimal intersection of a pedicle screw with the human vertebra having the surface image represented by the image data.

Further, the model data set may represent the pedicle screw by a direction of the pedicle screw model with respect to the model surface of the human vertebra model. The direction of the pedicle screw is also correspondingly adapted, when adapting the model data set. Thus, the adapted model data set provides the necessary information in order to find an optimal direction of a real pedicle screw to be partly screwed into the human vertebra.

The model data set may represent the pedicle screw at least by a virtual exit point of the pedicle screw model out of the span of the model surface of the human vertebra model. The virtual exit point of the pedicle screw model is preferably not an actual exit point, where the pedicle screw model further intersects the model surface of the human vertebra model. Instead, the virtual exit point of the pedicle screw model may be used as a basis for determining the direction of the pedicle screw model, when having knowledge of the virtual entry point. Thus, the virtual entry point and the virtual exit point of the pedicle screw model may provide the information for arranging a pedicle screw within a real human vertebra. When adapting the model data set, the virtual exit point of the pedicle screw model is adapted correspondingly. Thus, an optimal virtual exit point remains optimal after the adaptation.

According to a preferred embodiment, the model data set further represents the pedicle screw model at least by a penetration depth of the pedicle screw model into the span of the model surface of the human vertebra model.

In an example, a penetration depth of the pedicle screw model is predetermined, such that a breakthrough of the first end section of the pedicle screw model is prevented. In particular, if the model data set further represents the pedicle screw model by a virtual exit point of the pedicle screw model, the virtual exit point is not reached by the first end section of the pedicle screw model. Instead, the penetration depth predefines, how deep the pedicle screw model penetrates into the span of the model surface of the human vertebra model. Further preferably, the second end section of the pedicle screw model extends outwardly of the model surface of the human vertebra model.

As a result of adapting the model data set, the penetration depth of the pedicle screw model will be adapted correspondingly. Thus, after the adaptation, the penetration depth of the pedicle screw model remains optimal with respect to the remaining adaptation of the model surface of the human vertebra model. In particular, a subsequent calculation of the penetration depth of the pedicle screw model is not necessarily needed. Instead, a single adaptation may be sufficient in order to provide an optimal placement of the pedicle screw model within the model surface of the human vertebra model. Consequently, all information for the placement of a real pedicle screw in a human vertebra having a surface image corresponding to the adapted model surface is provided with a single adaptation step.

According to a preferred embodiment, the model data set further represents the pedicle screw model at least by a diameter of the pedicle screw model.

The diameter of the pedicle screw model is preferably predetermined, such that a corresponding real pedicle screw would provide a sufficient or maximum anchorage in a pedicle of a human vertebra having a surface image corresponding to the model surface of the human vertebra model. Further, the diameter of the pedicle screw model is preferably predetermined, such that a damaging of the pedicle of the human vertebra is effectively prevented under the same conditions, as stated before. Thus, the predetermined diameter may comprise an optimal compromise between an anchorage and a prevention of a damaging of a pedicle.

When adapting the model data set, the diameter of the pedicle screw is adapted correspondingly. Thus, a subsequent calculation of the diameter of the pedicle screw model is not necessary. Instead, a single adaptation of the model data set is sufficient.

According to a preferred embodiment, the model data set further represents the pedicle screw model at least by a screw thread parameter, in particular representing a class of fit, a screw thread depth and/or a screw taper.

Reference is made to the explanations, preferred features and/or effects provided with respect to the previously explained embodiments in an analogous manner. In particular, the screw thread parameter may be adapted in an analogous manner as the diameter of the pedicle screw model. Consequently, a predetermined screw thread parameter, being optimal with respect to the human vertebra model, remains optimal after the adaptation.

According to a preferred embodiment, the model data set further represents the pedicle screw model at least by a protrusion length representing a protrusion of the pedicle screw model out of the span of the model surface of the human vertebra model. In particular, the protrusion length corresponds to a length of the second end section of the pedicle screw model extending outwardly of the model surface of the human vertebra model.

The protrusion length may be optimal in the sense of an optimal compromise between accessibility and invasion of a real pedicle screw, when the real pedicle screw is placed in a real human vertebra based on the pedicle screw model. The accessibility preferably relates to the accessibility for connecting a connection rod to the second end section of the pedicle screw. The invasion may relate to the invasion of the second end section of the pedicle screw into the human area being next to the exit point of the pedicle screw out of the human vertebra.

By adapting the model data set, the protrusion length is adapted accordingly. Thus, an optimal protrusion length remains optimal when the model data set is adapted.

Even though the above provided embodiments have been exemplarily outlined for two, preferably adjacent, human vertebra, the device may be configured in an analogous manner for more than two human vertebra, if the image data represents more than two surface images.

According to a further aspect of the present invention, a method for planning a placement of pedicle screws is provided, comprising the steps of a), providing a global model data set representing a first model surface of a first human vertebra, a second model surface of a second human vertebra, a model arrangement of the first vertebra relative to the second vertebra, and first and second pedicle screw models being positioned in a pedicle section of the respective first and model surfaces;

b), receiving image data representing at least first and second vertebra images of respective first and second human vertebrae and an arrangement of the first and second surface images with respect to each other, and c), adapting the global model data set to the image data, such that an adapted model data set represents a first adapted model surface adapted to the first vertebra image, a second adapted model surface adapted to the second vertebra image and a correspondingly adapted model arrangement of the first adapted model surface relative to the second adapted model surface, wherein the adapted model data set also represents correspondingly adapted first and second pedicle screw models.

It is understood that, without repeating here all the explanations, examples, features and/or advantages provided with reference to the device, the method of the invention is intended to be configured to carry out the method steps for which the device is configured to. Thus, all the above examples, explanations, features and/or advantages, although provided with reference to the device, are also to be intended as being provided in an analogous manner for the method.

According to a third aspect of the present invention, a computer program element is provided, which, when being executed by a processing unit, is adapted to carry out the method described above.

According to a fourth aspect of the present invention, a computer-readable medium having stored thereon the program element is provided, which, when being executed by a processing unit, is adapted to carry out the method described above.

These and other aspects of the present invention will become apparent from and be elucidated with respect to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
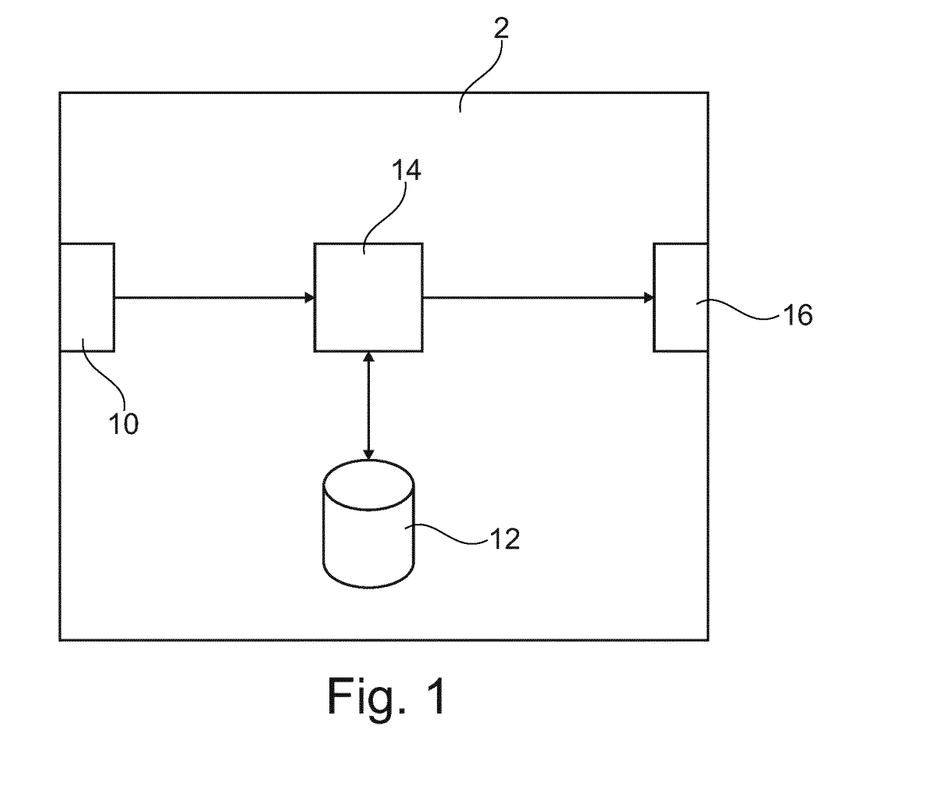
FIG. 1 schematically illustrates an embodiment of the device.

FIG. 1 schematically illustrates the device 2 for a determination of an optimal placement of a pedicle screw 4 in a human vertebra 6 during a spinal fusion procedure. A pedicle screw 4 must be placed with precision into a pedicle of a human vertebra 6 in order to avoid damaging of the human vertebra structure and at the same time to provide a sufficient anchor effect. In particular, pedicle screws 4 are inserted through a patient's back into adjacent vertebra, wherein the pedicle screws inserted into adjacent vertebra are connected by a connecting rod in order to generate a fixed bridge.

The device 2 is configured to provide an adapted data set, which can provide the relevant information for determining an optimal placement of said pedicle screws 4, such that the above provided requirements are fulfilled.

For this purpose, the device 2 may comprise an input interface 10, which is configured to receive data, in particular image data.

Further, the device 2 may comprise a storage means 12. The storage means 12 is configured to store data. In particular, the storage means 12 is configured to store a model data set and/or image data.

The input interface 10 may be further configured to receive a model data set. The model data set is a collection of data. The data, in particular the image data and/or the model data set, may be received by the input interface 10 and stored thereafter at the storage means 12.

The device 2 comprises a processing unit 14. Preferably, the processing unit 14 is configured to transmit data received via the input interface 10 to the storage means 12. Further, the processing unit 14 may be configured to receive data from the storage means 12.

Results of a process performed by the processing unit 14, in particular data and/or a data set, may be provided for further purpose via an output interface 16.

Figure 2:
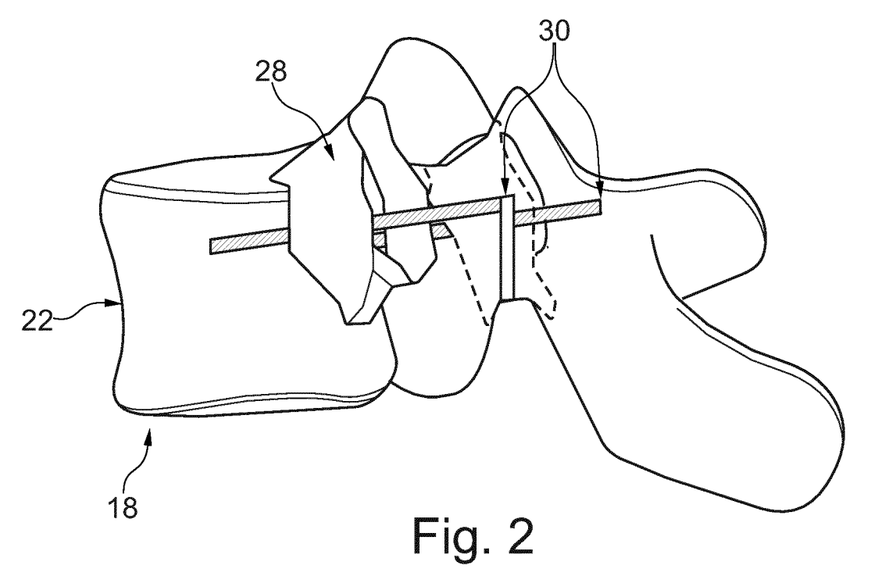
FIG. 2 schematically illustrates a human vertebra model.

FIG. 2 schematically illustrates a human vertebra model 18. The human vertebra model 18 may be formed by a triangulated mesh. The triangulated mesh may also form the interior of the human vertebra model 18. Preferably, the triangulated mesh further defines a surface, further called the model surface 22, of the human vertebra model 18. Thus, the model surface 22 may be formed by a plurality of points, which form the outer points of the triangulated mesh. However, the model surface 22 may be formed by another configuration of point at the surface of the human vertebra model 18.

The human vertebra model 18 is a three-dimensional human vertebra model 18. Consequently, the model surface 22 is also a three-dimensional model surface 22.

A human vertebra 6 usually has two pedicles 24. The human vertebra 6 of a spinal column as well as the respective pedicles 24 of the human vertebra 6 usually vary in size, shape and/or other dimensions.

The human vertebra model 18 schematically illustrated in FIG. 2 therefore just represents a model of an arbitrary human vertebra 6 or of an average of a plurality of arbitrary human vertebra 6. The pedicle section 28 of the model surface 22 of the human vertebra model 18 has been indicated in FIG. 2.

Further, FIG. 2 schematically illustrates two rods, each indicating a pedicle screw model 30. Each pedicle screw model 30 is extending from outside through the model surface 22 into the span of the model surface 22. The span of the model surface 22 refers to the interior space enclosed by the model surface 22.

With respect to a combination of FIGS. 1 and 2, the processing unit 14 is configured to receive a model data set representing a model surface 22 of a human vertebra model 18 and a pedicle screw model 30 being positioned in a span of a pedicle section 28 of the model surface 22. As a result, the processing unit 14 receives the information where and how to place a pedicle screw 4 into a pedicle section of a human vertebra 6, if the human vertebra 6 corresponds to the human vertebra model 18. In practice, this is however a rather rare case. Usually, each human vertebra 6 has its own surface, which liked do not match the model surface 22 of the human vertebra model 18. Thus, an adaptation of the model surface 22 and the related pedicle screw model 30 would be needed, in order to serve as an information basis for optimally placing a pedicle screw.

However, before using the processing unit for performing the adaptation, a determination of a surface image of the human vertebra is needed. In order to determine such a surface image of a real human vertebra, medical imaging devices, such as computer tomography (CT), magnetic resonance imaging (MRI) or one of the other already named medical imaging devices, or a combination thereof, may be used for capturing a surface image of a real human vertebra.

Figure 3:
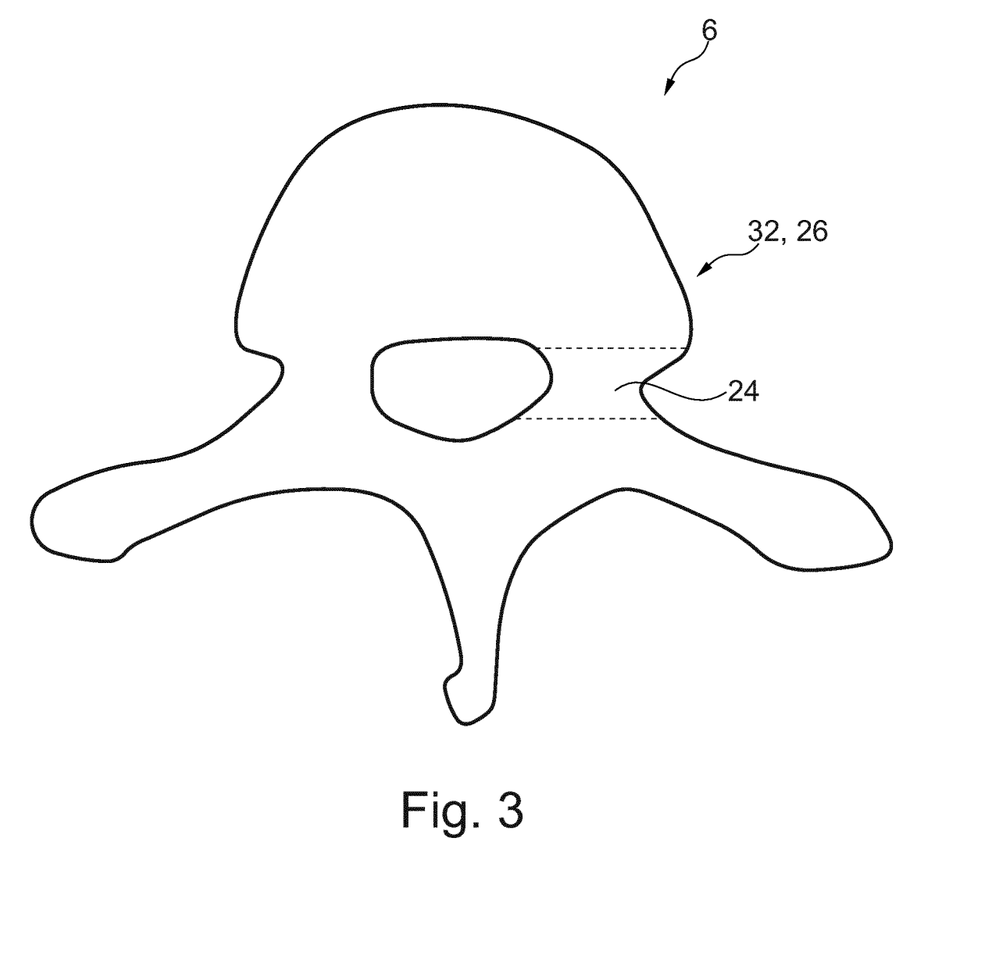
FIG. 3 schematically illustrates a surface image of a human vertebra in a cross-sectional view.

For simplicity reasons, FIG. 3 schematically illustrates a cross-sectional view of a surface image of a human vertebra 6, wherein the outer line 32 indicates a surrounding line of the human vertebra 6. The processing unit 14 is configured to receive image data representing a surface image of at least one human vertebra 6.

Figure 4:
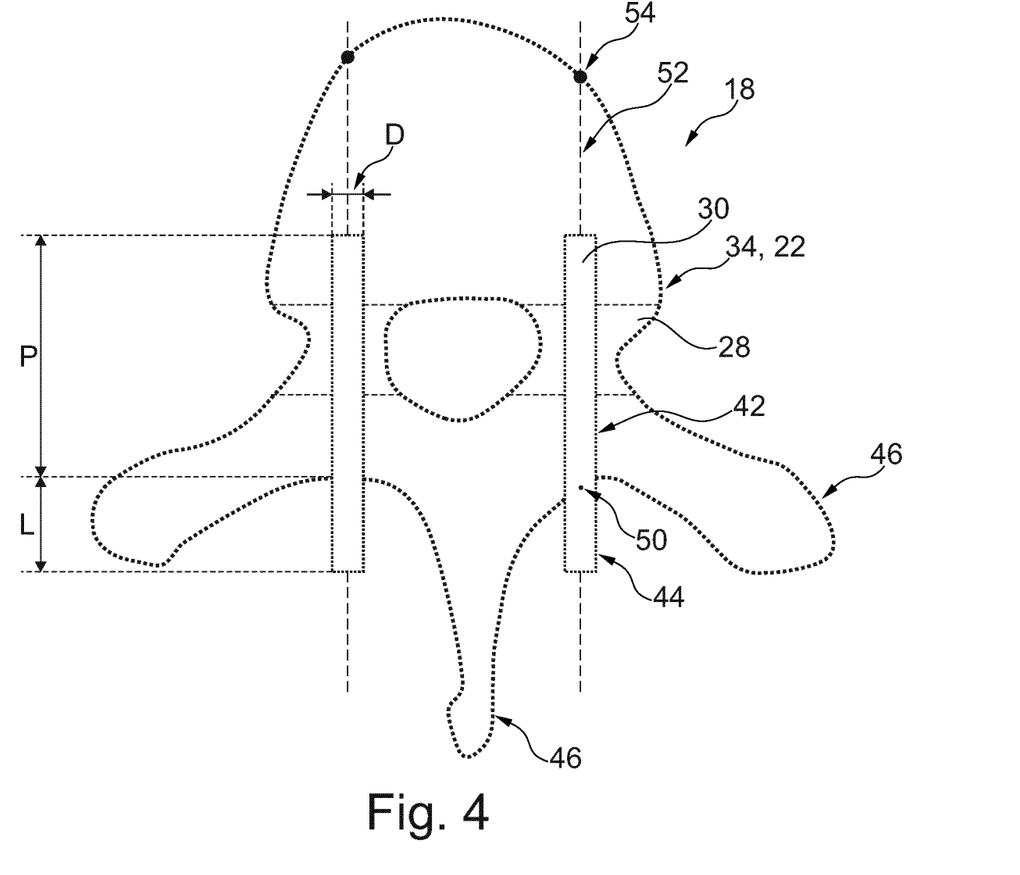
FIG. 4 schematically illustrates a model surface of a human vertebra model in a cross-sectional view.

In an analogous manner as described with respect to FIG. 3, FIG. 4 schematically illustrates a cross-sectional view of a model surface 22 of the human vertebra model 18, wherein the outer line 34 indicates a surrounding line of the human vertebra model 18. Further, FIG. 4 schematically illustrates the pedicle sections 28 of the model surface 22 of the human vertebra model 18 as well as the pedicle screw model 30.

In an example, the pedicle screw model 30 may at least partly be formed by a set of points. In particular, the set of points may correspond to the points of the dotted line indicating in FIG. 4 the pedicle screw model 30. Alternatively, pedicle screw model 30 may at least partly be formed by a plurality of points, which are preferably characteristic for the representation of a surface of the pedicle screw model 30. Respective characteristic points may be a point at each end or end section of a pedicle screw, which the pedicle screw model 30 is supposed to represent. Further characteristic points may refer to lateral surface section, for instance to represent a diameter of the pedicle screw, which the pedicle screw model 30 is supposed to represent.

As can be seen from FIG. 4, each pedicle screw model 30 is spaced apart from the pedicle section 28 of the model surface 22, in order to provide a good anchor effect and further to prevent a damaging, if the model data set is used as an information-basis for placing a real pedicle screw. Even though the indicated pedicle screw model 30 is optimally placed in a span of the pedicle section 28 of the model surface 22 of the human vertebra model 18, this representation cannot be directly used for implementing pedicle screws into a real human vertebra 6.

However, the processing unit 14 is configured to adapt the model data set for a human vertebra 6, such that an adapted model data set represents a correspondingly adapted model surface 36, which fits to the surface image 26 of the respective human vertebra 6, wherein the adapted model data set also represents a correspondingly adapted pedicle screw model 38. In case several human vertebras 6 are supposed to be subject to an implantation of pedicle screws 4, the aforementioned adaptation may be carried out by means of the processing unit 14 for each of the human vertebras 6.

Figure 5:
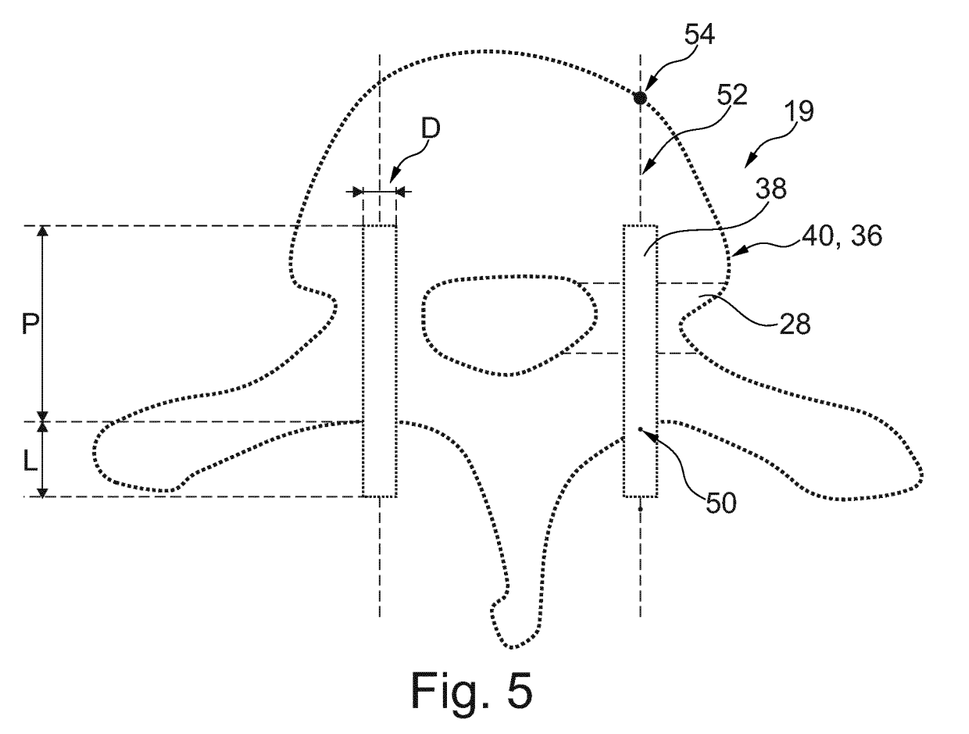
FIG. 5 schematically illustrates an adapted model surface in a cross-sectional view.

FIG. 5 schematically illustrates a cross-sectional representation of an adapted human vertebra model 19 after an adaptation of the model data set resulting in the adapted model data set. The adapted model data set represents the adapted model surface 36 and the adapted pedicle screw model 38. As can be seen from a synopsis of FIGS. 3 to 5, the outer line 40 indicating the adapted model surface 36 has been adapted, such that it fits to the outer line 32, shown in FIG. 3, indicating the surface image 26 of the human vertebra 6. Thus, the adaptation of the model data set has been performed, such that a deformation of the model surface 22 is carried out in order to fit to the surface image 26 of the human vertebra 6. Further, applying the adaptation to the whole model data set will in analogous manner cause a deformation of the pedicle screw model 30 resulting in the adapted pedicle screw model 38. As a consequence, the placement of the adapted pedicle screw 38 will remain optimal. In detail, the adapted pedicle screw model 38 is optimally placed in the span of the pedicle section 28 of the adapted model surface 36. For an illustration purpose, FIG. 5 schematically shows adapted dimensions for the adapted pedicle screw model 36.

Since the adapted model surface 36 fits to the surface image 26 of the human vertebra 6, the adapted model data set provides the information for optimally placing a real pedicle screw into a pedicle 24 of the human vertebra 6.

Figure 6:
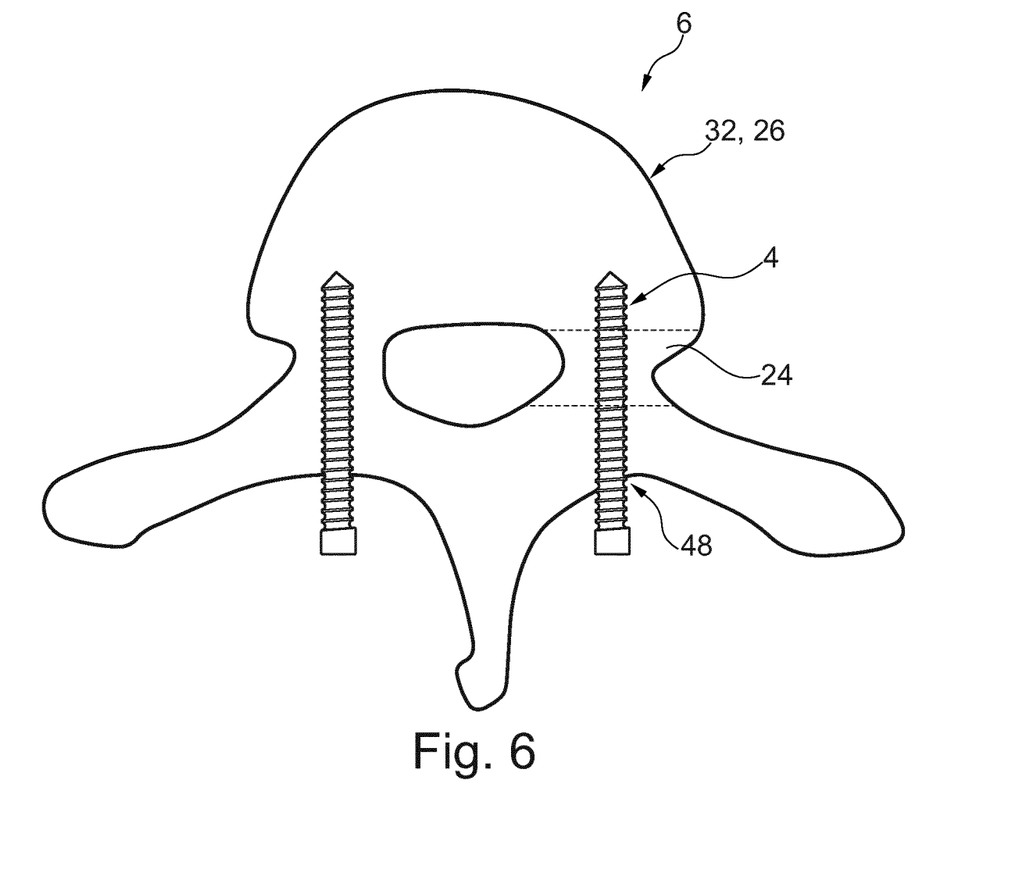
FIG. 6 schematically illustrates the model surface of FIG. 4 with indicated pedicle screws in a cross-sectional view.

FIG. 6 schematically illustrates the human vertebra 6 as before in FIG. 3, wherein based on the information provided by the adapted model data set, pedicle screws 4 have been implanted into the pedicles 24 of the human vertebra 6.

As a result of the use of the device 2 comprising the processing unit 14, the model data set may be used for a plurality of human vertebra 6 in order to provide the information for an optimal placement of pedicle screws 4 into respective pedicles 24. Even though the structure of each human vertebra 6, and in particular their respective surface 26, may vary from one to another, the same model data set may be used each time for an optimal placement of the pedicle screw 4. A subsequent analysis of each of the plurality of human vertebra 6, and in particular carrying out each time a sub-analysis of the respective surface image 6 and/or of the structure and/or width of the respective pedicle 24, can be prevented. Thus, for each of a plurality of human vertebra 6, it is just an adaptation what is each time needed, in order to provide the necessary information for an optimal placement of a pedicle screw 4. As an effect, less processing power is needed and reproducible results can be provided.

As can be seen from FIG. 4, the pedicle screw model 30 is located with its first end section 42 within the span of the model surface 22 of the human vertebra model 18. Preferably, a part of this first end section 42, also referred to as an intermediate section 43, is located within the pedicle section 28 of the model surface 22 of the human vertebra model 18. A second end section 44 of the pedicle screw model 30 protrudes out of the model surface 22 of the human vertebra model 18. As the pedicle screw model 30 is represented by the model data set, the same holds for its sections 42, 43, 44. Thus, when adapting the model data set in order to provide a fit between the model surface 22 and the image surface 26, a corresponding adaptation is carried out for the sections 42, 43, 44 of the pedicle screw model 30. As an effect, an optimal placement of the first end section 42, of the intermediate section 43, and/or the second end section 44 of the pedicle screw model 30 remains optimal, if the model data set is adapted, as explained above.

As can be seen from FIGS. 2 and 4, the model data set may represent the model surface 22 of the human vertebra model 18 and two pedicle screw models 30, each being optimally placed in a span of a pedicle section 28 of the model surface 22. During the adaptation of the model data set, both pedicle screw models 30 are adapted correspondingly, such that each of the adapted pedicle screw models 38 remains optimally placed in a span of a respective pedicle section 28 of the adapted model surface 36.

In order to provide a good accessibility of a pedicle screw 4, if it is placed in a human vertebra 6 based on the information provided by the model data set or the adapted model data set, a respective arrangement and/or dimension of the pedicle screw model 30 should provide a respective information basis. Therefore, according to a preferred embodiment, the model data set represents the pedicle screw model, such that it is arranged between two, outwardly extending surface sections 46 of the model surface 22 representing processes of the human vertebra model 18. It has been found, that such a location of the second end section 44 of the pedicle screw model 30 provides good accessibility for connecting a connecting rod to the second end section 44 of the pedicle screw 4, in case a respective pedicle screw 4 is implemented in human vertebra 6 based on the information provided by the model data set. As explained above in analogous manner, an adapted model data set would not affect the good accessibility.

It is further preferred, that the pedicle screw model 30, represented by the model data set, is arranged with respect to the model surface 22 of the human vertebra model 18, such that the second end section 44 of the pedicle screw model 30 is not in vertical overlap with one of the outwardly extending surface sections 46 of the model surface 22 representing the processes of the human vertebra model 18. Such a placement of the pedicle screw model 30 even further ensures a possible direct connection of two pedicle screws 4 being placed in adjacent human vertebras 6, when using the information of the adapted model data set for each placement of the respective pedicle screw 4. In this case, a collision between a connecting rod and processes of a human vertebras 6 is effectively prevented.

For inserting a pedicle screw 4 into a human vertebra 6, it has been found in practice, that one helpful information is the so-called entry point 48, as indicated in FIG. 6. The entry point 48 refers to the point on the surface of the human vertebra 6, where the pedicle screw 4 is supposed to be inserted into the interior of the human vertebra 6. It is therefore a preferred embodiment of the present invention, that the model data set represents the pedicle screw model 30 at least by a virtual entry point 50 of the pedicle screw model 30 into the span of the model surface 22 of the human vertebra model 18. The virtual entry point 50 gives the information, where a respective pedicle screw 4 is supposed to be entered, in case the pedicle screw model 30 is used for implementing the pedicle screw 4. As the model data set is adapted also for the pedicle screw model 30 resulting in an adapted pedicle screw model 38, the virtual entry point 50 is adapted in an analogous manner, such that the adapted model data set provides the respective information, where the pedicle screw 4 is to be inserted, when using the adapted model data set as a basis for the implantation of the pedicle screw 4.

According to a further preferred embodiment, the model data set represents the pedicle screw model at least by a direction 52 of the pedicle screw model 30 with respect to the model surface 22 of the human vertebra model 18. The direction 52 of the pedicle screw model 30 is indicated in FIG. 4 as a dashed line. As can be seen from the FIG. 4, the virtual entry point 50 may form a point on the direction line 52. Thus, having notice of the virtual entry point 50 and the direction 52, a person who wants to implant a real pedicle screw 4 to a human vertebra 6 based on the information provided by the model data set, will receive the information, where and how to implant the pedicle screw 4 into the human vertebra 6, if the human vertebra 6 corresponds to the human vertebra model 18. As explained above, however, usually the model surface 22 of the human vertebra model 18 has to be adapted, in order to fit to the image surface 26 of the human vertebra 6, where the pedicle screw 4 has to be implanted.

FIG. 5 schematically illustrates the result of an adapted model data set, wherein the direction 52 and the virtual entry point 50 are adapted correspondingly. With reference to the previous explanations, the virtual entry point 50 and the direction 52 remain optimal. Using this information for implementing the pedicle screw 4 into the human vertebra 6, a respective optimal placement of the pedicle screw 4, as shown in FIG. 6, can be provided.

According to a further preferred embodiment, the model data set represents the pedicle screw model 30 at least by a virtual exit point 54 of the pedicle screw model 30 out of the span of the model surface 22 of the human vertebra model 18. The virtual exit point 54 is not a point, where the pedicle screw model 30 is supposed to be extending outward of the model surface 22. Instead, the virtual exit point 54 is rather an auxiliary point, which allows to give an information about the orientation of the pedicle screw model 30, or the pedicle screw 4, if this information is used for implanting the pedicle screw 4 into a human vertebra 6. As explained before, the model data set will be adapted, such that the model surface 22 fits to the image surface 26, wherein the adaptation is carried out in an analogous manner for the virtual exit point 54. As can be seen from FIG. 5, a correspondingly adapted virtual exit point 54 remains optimal after the adaptation of the model data set resulting in the adapted model data set. In particular, the virtual exit point 54 is a point on the direction line 52.

In practice, it has been found that at least two of the virtual entry point 50, the direction 52 and the virtual exit point 54 may be sufficient for an optimal placement of a pedicle screw 4 into a human vertebra 6 based on the information provided by the adapted model data set. Accordingly, respective a sub-data set of the model data set and/or of the adapted model data set may be kept small, which allows to carry out the adaptation in less time.

According to a further preferred embodiment, the model data set represents the pedicle screw model 30 at least by a penetration depth P of the pedicle screw model 30 into the span of the model surface 22 of the human vertebra model 18.

According to a further preferred embodiment, the model data set represents a pedicle screw model at least by a diameter D of the pedicle screw model 30.

According to a further preferred embodiment, the model data set represent the pedicle screw model 30 at least by a protrusion length L representing a protrusion of the pedicle screw model out of the span of the surface model 22 of the human vertebra model 18.

Each of the three previously described embodiments of the invention provide the effect, that the pedicle screw model 30 may be represented by the model data set in more detail. These details relate to the penetration depth P, the diameter D and/or the protrusion length L. As explained in an analogous manner before, an adaptation of the model data set resulting in an adapted model data set will result in an analogous adaptation of the penetration depth P, the diameter D and/or the protrusion length L. Respective adaptations of the penetration depth P, the diameter D and the protrusion length L are indicated in FIG. 5, which represent an adapted human vertebra model 19.

With respect to FIG. 2, it has been described, that the model data set represent a model surface 22 of a human vertebra model 18 and a pedicle screw model 30 being optimally placed in a span of a pedicle section 28 of the model surface 22. In practice, medical imaging devices may be configured to acquire an image of more than one human vertebra 6. Thus, the image data received by the processing unit 14 may represent respective surface images 26 of more than one human vertebra 6. In particular, the image data may represent a first surface image of a first human vertebra and a second surface image of a second human vertebra.

Figure 7:
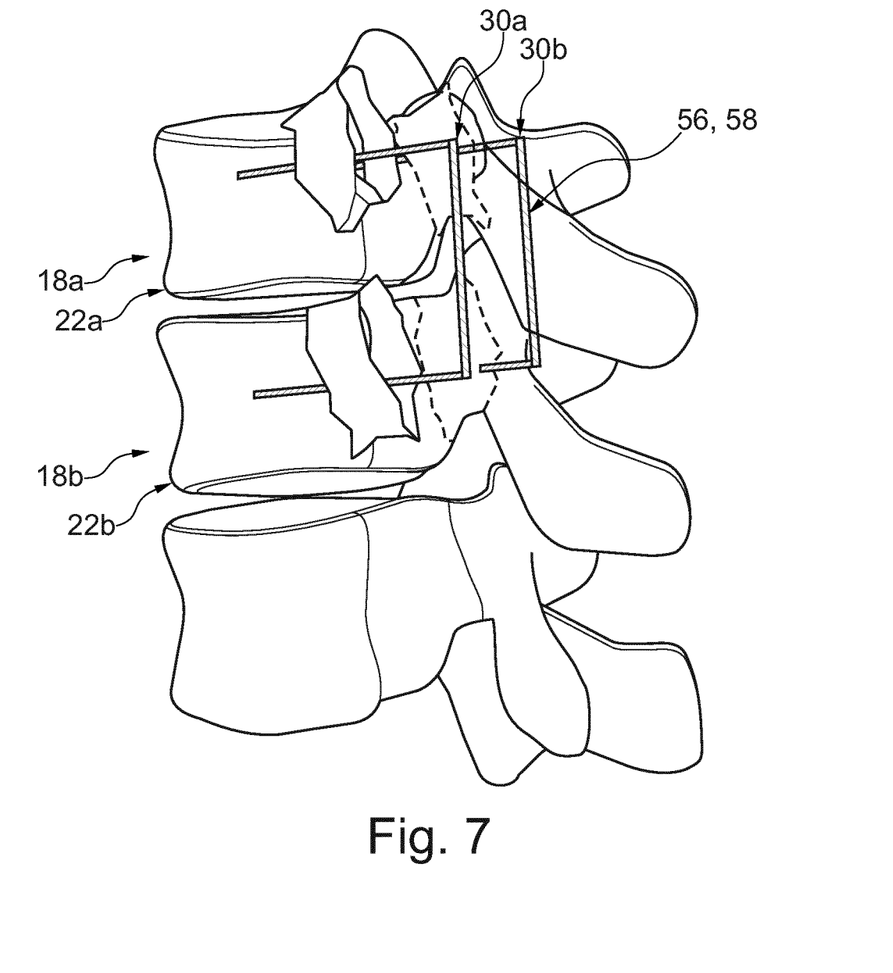
FIG. 7 schematically illustrates an arrangement of a plurality of a human vertebra models.

In particular, the processing unit 14 is configured to adapt the global model data set to the image data, such that a first adapted model surface 22a is adapted to the first image of the first human vertebra, is provided, wherein the adapted model data set also represents a correspondingly adapted first adapted pedicle screw model 30a. Further, a second adapted model surface 22b is adapted to the second image of the second human vertebra, wherein the adapted model data set also represents a correspondingly adapted second adapted pedicle screw model 30b.

The image data also represents an arrangement of the vertebra images relative to each other. This arrangement information may refer to the orientation of a first image relative to the second image. Furthermore, the global model data set further represents a model arrangement of the first vertebra 18a relative to the second vertebra 18b. The model arrangement thus may provide the information, how the individual vertebrae 18a, 18b along the human spine are oriented and/or placed relative to each other.

Further, the processing unit 14 is configured to adapt the global model data set so that the adapted model data set represents a correspondingly adapted model arrangement of the first adapted model surface relative to the second adapted model surface. In other words, in adapting the model data set to the image data, the model arrangement, i.e. global model data, are taken into consideration as an additional constraint in determining an adaptation of the local vertebra surface models to the individual vertebra images or image portions.

As a result, the adapted global model data set provides the information, how and where to place pedicle screws 4 at two human vertebras 6, which are preferably adjacent to each other.

According to a further embodiment of the invention, the global model data set further represents a connecting rod model 56 extending from the first pedicle screw model 30a to the second pedicle screw model 30b, wherein the processing unit 14 is configured to adapt the connecting rod model based on the adaptation of the model arrangement resulting in an adapted connecting rod model extending from the first adapted screw model to the second adapted screw model, and wherein the adapted global model data set further represents the adapted connecting rod model.

In an example, the connecting rod model 56 represents a length, a diameter, an orientation and/or a location of a connecting rod configured to connect two pedicle screws 4, which are supposed to be implanted into adjacent human vertebras 6.

As a result, the adapted global model data set may further provide the information about the form of the connection rod and/or where to place a connection rod.

In an example, the connection rod model 56 may represent a form of a connection rod. For instance, the connection rod model 56 may represent a straight form of a connection rod. However, a connection rod may have a curved form. In this case, connection rod model 56 may represent a curved form of a connection rod. Generally, the connection rod model 56 may represent an arbitrary form of a connection rod.

Figure 8:
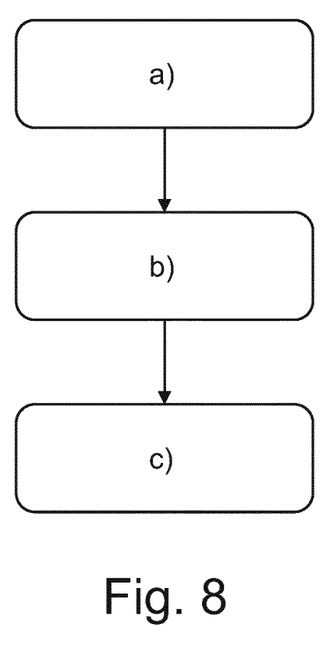
FIG. 8 schematically illustrates a flow-chart of the method according to the present invention.

FIG. 8 schematically illustrates a flow-chart of a method for an optimal placement of a pedicle screw 4 according to the present invention. The method comprised the following:

In a step a), providing a global model data set representing a first model surface of a first human vertebra, a second model surface of a second human vertebra, a model arrangement of the first vertebra relative to the second vertebra, and first and second pedicle screw models being positioned in a pedicle section of the respective first and model surfaces.

In a step b), receiving image data representing at least first and second vertebra images of respective first and second human vertebrae and an arrangement of the first and second surface images with respect to each other.

In a step c), adapting the global model data set to the image data, such that an adapted model data set represents a first adapted model surface adapted to the first vertebra image, a second adapted model surface adapted to the second vertebra image and a correspondingly adapted model arrangement of the first adapted model surface relative to the second adapted model surface, wherein the adapted model data set also represents correspondingly adapted first and second pedicle screw models.

According to a further example of the present invention, a computer program element is provided, which, when being executed by a processing unit is adapted to carry out the method described above.

According to further example of the present invention, a computer readable medium having stored thereon a program element is provided, which, when being executed by a processing unit is adapted to carry out the method described above.

The computer program element might be stored on a computer unit, which might also be part of an embodiment of the present invention. This computing unit may be adapted to perform or induce a performing of the steps of the method described above. Moreover, it may be adapted to operate the components of the above described device. The computing unit can be adapted to operate automatically and/or to execute the orders of a user. A computer program may be loaded into a working memory of a data processor. The data processor may thus be equipped to carry out the method of the invention.

It has to be noted that embodiments of the invention are described with reference to different subject matters. In particular, some embodiments are described with reference to the method whereas other embodiments are described with reference to the device. However, a person skilled in the art will gather from the above that, unless otherwise notified, in addition to any combination of features belonging to one embodiment also any combination between features relating to different embodiments is considered to be disclosed with this application.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. Any reference signs in the claims should not be construed as limiting the scope.

The invention claimed is:

1. A device for planning a placement of pedicle screws, comprising:
    a processing unit,
    wherein the processing unit is configured to receive a global model data set representing:
        a first model surface of a first human vertebra and a first pedicle screw model positioned in a pedicle section of the first model surface,
        a second model surface of a second human vertebra and a second pedicle screw model positioned in a pedicle section of the second model surface, and
        a model arrangement of the first human vertebra relative to the second human vertebra,
    wherein the processing unit is configured to receive image data representing at least a first image of a first human vertebra, a second image of a second human vertebra and an arrangement of the first image relative to the second image,
    wherein the processing unit is configured to adapt the global model data set to the image data, the adapted model data set representing:
        a first adapted model surface adapted to the first image of the first human vertebra,
        a second adapted model surface adapted to the second image of the second human vertebra, and
        a correspondingly adapted model arrangement of the first adapted model surface relative to the second adapted model surface,
    wherein the adapted model data set further represents correspondingly adapted first and second pedicle screw models.

2. The device according to claim 1,
    wherein the global model data set further represents a connecting rod model extending from the first pedicle screw model to the second pedicle screw model,
    wherein the processing unit is configured to adapt the connecting rod model based on the adaptation of the model arrangement resulting in an adapted connecting rod model extending from the first adapted pedicle screw model to the second adapted pedicle screw model, and
    wherein the adapted model data set further represents the adapted connecting rod model.

3. The device according to claim 2, wherein the connecting rod model represents a length, a diameter, an orientation and/or a location of a connecting rod configured to connect two pedicle screws to be implanted into adjacent human vertebrae.

4. The device according to claim 1, wherein a first end section of a the adapted first pedicle screw model is positioned within a span of the first adapted model surface and a second end section of the adapted first pedicle screw model protrudes out of said first adapted model surface,
    and wherein a first end section of the adapted second pedicle screw model is positioned within a span of the second adapted model surface, and a second end section of the adapted second pedicle screw model protrudes out of said second adapted model surface.

5. The device according to claim 1, wherein the global model data set represents the first pedicle screw model at least by two of: a virtual entry point of the first pedicle screw model into a span of the first model surface of a first human vertebra model, a direction of the first pedicle screw model with respect to the first model surface of the first human vertebra model, and a virtual exit point of the first pedicle screw model out of the span of the first model surface of the first human vertebra model,
    and wherein the global model data set represents the second pedicle screw model at least by two of: a virtual entry point of the second pedicle screw model into a span of the second model surface of a second human vertebra model, a direction of the second pedicle screw model with respect to the second model surface of the second human vertebra model, and a virtual exit point of the second pedicle screw model out of the span of the second model surface of the second human vertebra model. model further includes a penetration depth of the first pedicle screw model into the span of the first model surface,
    and wherein the second pedicle screw model further includes a penetration depth of the second pedicle screw model into the span of the second model surface.

6. The device according to claim 5, wherein the first pedicle screw model further includes a penetration depth of the first pedicle screw model into the span of the first model surface,
    and wherein the second pedicle screw model further includes a penetration depth of the second pedicle screw model into the span of the second model surface.

7. The device according to claim 5, wherein the first pedicle screw model further includes a diameter D of the first pedicle screw model and/or a screw thread parameter of the first pedicle screw model, and wherein the second pedicle screw model further includes a diameter D of the second pedicle screw model and/or a screw thread parameter of the second pedicle screw model.

8. The device according to claim 4, wherein the first pedicle screw model further includes a protrusion length L of the second end portion of the first pedicle screw model, and wherein the second pedicle screw model further includes a protrusion length L of the second end portion of the second pedicle screw model.

9. A method for planning a placement of pedicle screws, comprising the following steps:

a) providing a global model data set representing a first model surface of a first human vertebra, a second model surface of a second human vertebra, a model arrangement of the first vertebra relative to the second vertebra, and first and second pedicle screw models being positioned in a pedicle section of the respective first and second model surfaces;

b) receiving image data representing at least first and second vertebra images of respective first and second human vertebrae and an arrangement of first and second surface images of the first and second vertebra images with respect to each other; and c) adapting the global model data set to the image data, such that an adapted model data set represents a first adapted model surface adapted to the first vertebra image, a second adapted model surface adapted to the second vertebra image and a correspondingly adapted model arrangement of the first adapted model surface relative to the second adapted model surface, wherein the adapted model data set also represents correspondingly adapted first and second pedicle screw models.

10. A computer program element for controlling a device which, when being executed by a processing unit, is adapted to perform the method steps of claim 9.

11. A non-transitory computer-readable medium having stored the program element of claim 10.

* * * * *